United States Patent [19]

Racz et al.

[11] Patent Number: 4,637,394
[45] Date of Patent: Jan. 20, 1987

[54] CONSTANT PRESSURE TOURNIQUET

[76] Inventors: Gabor B. Racz, 4504 17th St., Lubbock, Tex. 79416; Royce C. Lewis, 5233 19th St., Lubbock, Tex. 79407

[21] Appl. No.: 743,566

[22] Filed: Jun. 11, 1985

[51] Int. Cl.$^4$ ............................................. A61B 17/12
[52] U.S. Cl. ................................................... 128/327
[58] Field of Search ............... 128/327, 686, DIG. 20, 128/678, 87

[56] References Cited

U.S. PATENT DOCUMENTS

| | | | |
|---|---|---|---|
| 1,269,620 | 6/1918 | Levine | 128/327 |
| 1,366,121 | 1/1921 | Dorsey | 128/327 |
| 1,679,978 | 8/1928 | Konwiser et al. | 128/327 |
| 1,827,241 | 10/1931 | Kempf | 128/327 |
| 2,031,870 | 2/1936 | Vertuno | 128/327 |
| 2,045,750 | 6/1936 | Buschenfeldt | 128/327 |
| 2,455,859 | 12/1948 | Foley | 128/327 |
| 2,511,269 | 6/1950 | Jones | 128/327 |
| 3,086,529 | 4/1963 | Munz et al. | 128/327 |
| 3,120,846 | 2/1964 | Fletcher | 128/327 |
| 3,548,819 | 12/1970 | Davis | 128/DIG. 20 |
| 3,570,495 | 3/1971 | Wright | 128/327 |
| 3,633,567 | 1/1972 | Sarnoff | 128/327 |
| 3,654,931 | 4/1972 | Hazlewood | 128/327 |
| 3,756,239 | 9/1973 | Smythe | 128/327 |
| 3,906,937 | 9/1975 | Aronson | 128/327 |
| 4,106,499 | 8/1978 | Ueda | 128/327 |
| 4,210,147 | 7/1980 | Nestor et al. | 128/327 |
| 4,228,792 | 10/1980 | Rhys-Davis | 128/327 |

Primary Examiner—Robert Peshock
Assistant Examiner—Cary E. Stone
Attorney, Agent, or Firm—Marcus L. Bates

[57] ABSTRACT

A constant pressure tourniquet has an interior chamber formed therein by a continuous wall surface. The wall of the tourniquet is made of an expansible elastomeric material. The chamber is inflated with a suitable fluid to a pressure in excess of the threshold pressure provided by the elastomeric material. The tourniquet preferably is of annular or rectangular configuration, and can be adjustably arranged to effectively form a toroidal void within which a pressure producing fluid is contained. The tourniquet is made in various different sizes and configurations, and includes overlapping marginal ends which are fastened together and thereby provides a suitable inside diameter for proper placement about one's limb, such as a finger, arm, or leg, for example. The physical characteristics exhibited by the elastomer are selected to provide the required internal pressure for preventing bleeding. The internal pressure and size of the tourniquet therefore is selected to prevent bleeding of that part of the anatomy that receives the tourniquet.

18 Claims, 14 Drawing Figures

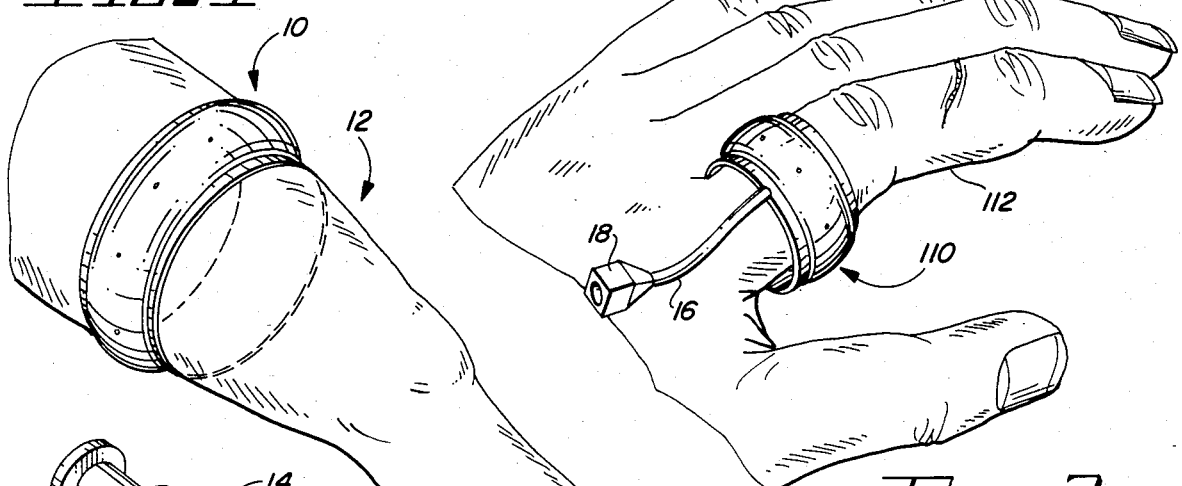
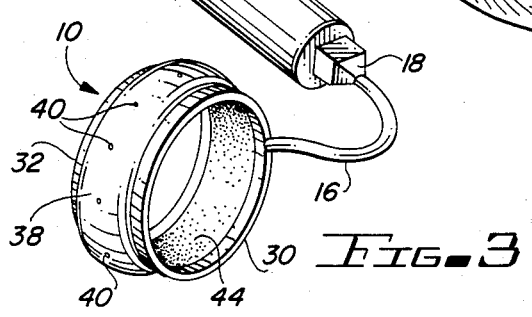
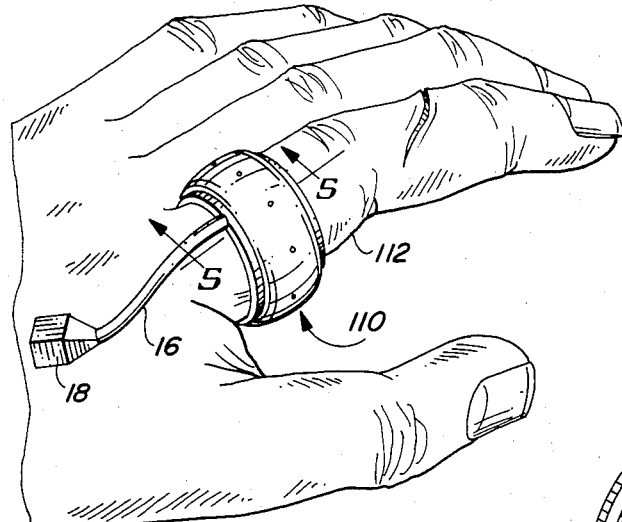
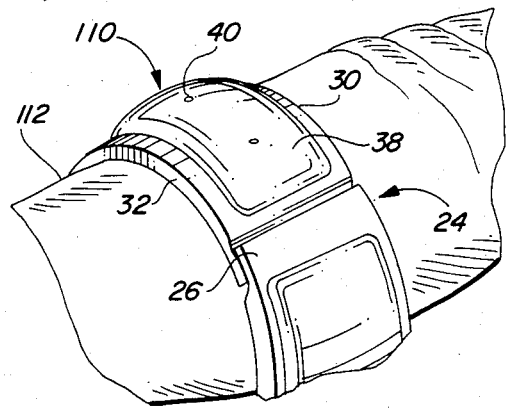
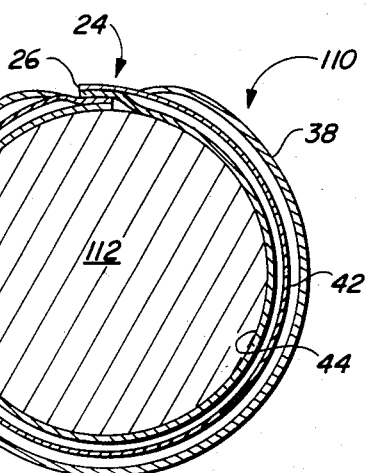
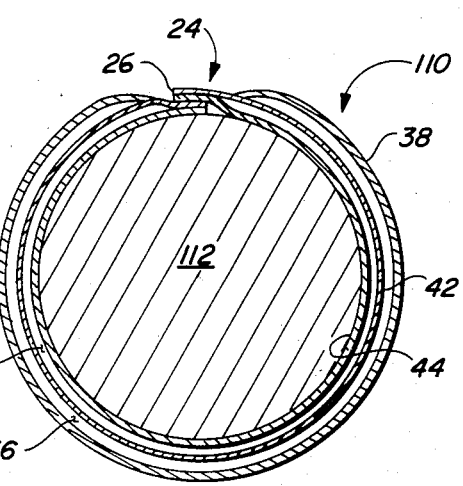

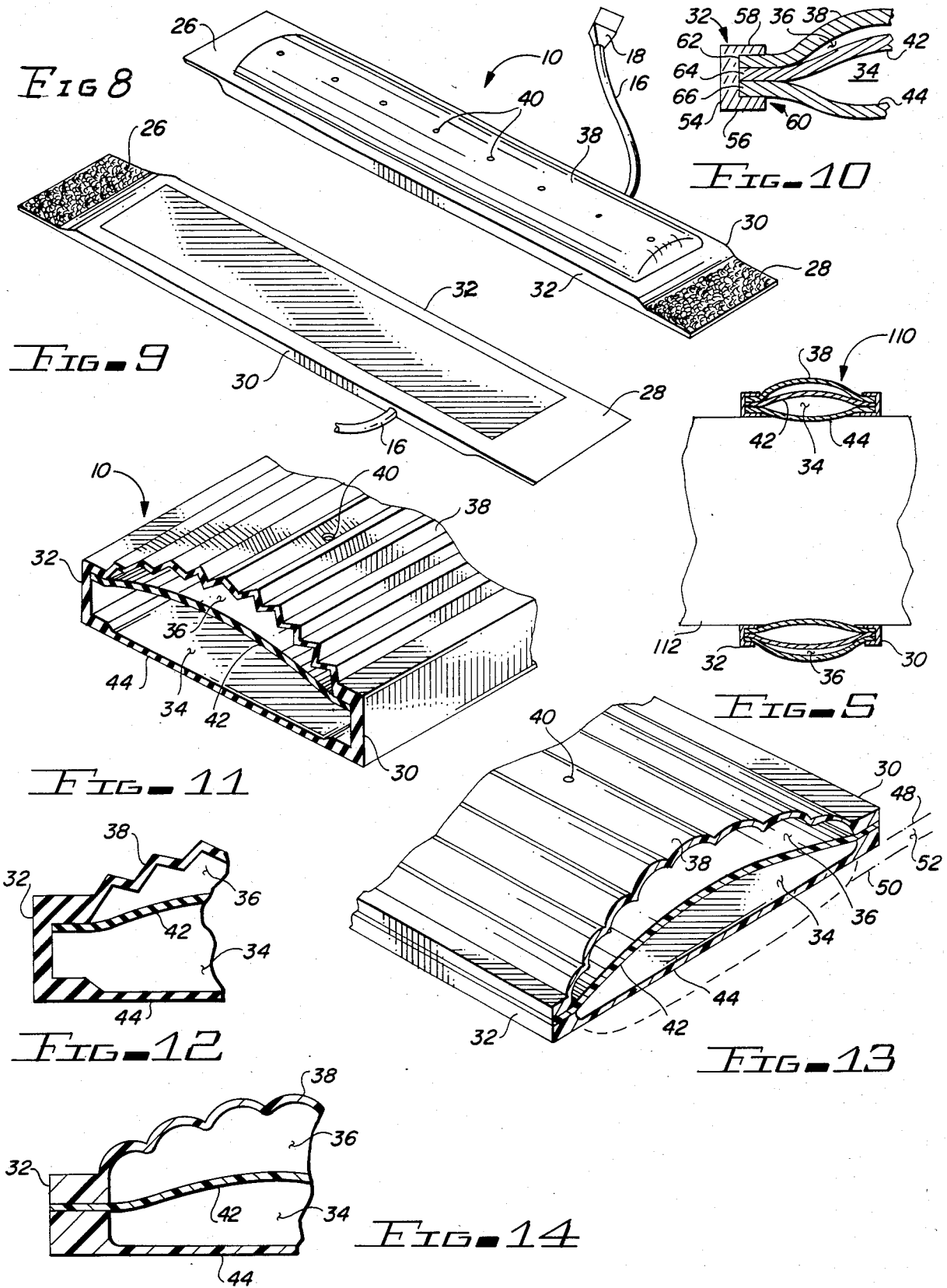

CONSTANT PRESSURE TOURNIQUET

BACKGROUND OF THE INVENTION

Pneumatically inflated tourniquets are known to those skilled in the art as evidenced by the U.S. Pat. Nos. 2,511,269; to Jones, 1,366,121; to Dorsey, 1,679,978; to Konwiser, et al 1,827,241; to Kempf, 3,086,529; to Munz, et al 2,031,870; to Vertuno, 2,045,750; to Buschenfeldt, 3,654,931; to Hazelwood, 3,906,937; to Aronson 4,210,147; to Nestor, et al 4,106,499; to Ueda 3,633,567; to Sarnoff and 3,120,846 to Fletcher. In each of these U. S. Patents, an inflatable tourniquet is wrapped about the limb and subsequently fastened, after which pneumatic pressure is forced into a bladder or chamber contained within the tourniquet.

U.S. Pat. No. 1,269,620 to Levine provides a tourniquet which can be slipped over one's limb. The tourniquet is an endless tubing having a lateral passageway connected thereto for increasing the internal pressure of the tubing.

U.S. Pat. No. 4,228,792 to Rhys-Davies proposes a fluid filled envelop in the form of a double wall tube of elastomer wherein the inner and outer walls are maintained below a threshold pressure. The cylindrical member can be secured on one's limb and is employed for forcing blood from a patient's limb.

It is possible to make an elastomeric toroidal member of a size to be received about one's finger, arm, or leg, wherein the thickness of the elastomeric wall of the toroid is selected along with the modulus of elasticity whereby continued inflation of the interior of the toroid will exceed a threshold value, whereupon further inflation will expand the toroid walls without a proportional increase in the interior pressure of the toroid.

It is desirable to have made available a tourniquet which can be placed about the extremity of a person's anatomy, such as a person's limb, by simply forcing the tourniquet into place at the desired location on the person's body. It would be desirable that such a tourniquet be previously inflated to the required internal pressure which precludes loss of blood from an injury associated with the limb. A tourniquet device which achieves these desirable goals is the subject of the present invention.

The elastomer of the novel tourniquet disclosed herein can be obtained from natural sources or synthesized artificially. The elastomer preferably is compounded and made into a selected thickness to impart the desirable properties of extensibility, stretchability, and toughness. Modulus is normally a function of the state of cure or degree of vulcanization, and is considered more important than tensile strength. As used herein the term "modulus of elasticity" is intended to mean the measure of stretch or elongation exhibited by the rubber as the chamber of the tourniquet is inflated; and, the term "threshold pressure" means the psi which must be effected on the internal wall surface that forms the tourniquet chamber in order that the volume of the chamber commences expanding at substantially constant internal pressure.

For example, a rubber balloon is difficult to inflate as a first volume of air is introduced into the chamber thereof; however, as the volume is increased an internal pressure is reached wherein further increase in volume is achieved without any further increase in the pressure, or at least, the increase in pressure required to achieve the additional volume is not proportional to the first increase in pressure required to achieve the first increase in volume.

SUMMARY OF THE INVENTION

A previously inflated tourniquet is of a size to be removably received about a person's limb. The tourniquet is fabricated from relatively thin elastomeric material which forms a continuous wall surface and thereby defines a chamber.

The elastomeric material from which the chamber wall is made is of a selected thickness and modulus of elasticity that manifests an internal threshold pressure which is slightly greater than the blood pressure of the limb that requires the tourniquet.

The tourniquet of the preferred form of the invention is in the form of a flexible rectangular member having marginal ends which can be fastened together and thereby takes on the appearance of a doughnut or toroid. In one form of the invention, the tourniquet is adjustably fastened into a toroidal configuration and is positioned about one's finger at a location to arrest the flow of blood to and from the limb.

In another form of the invention, the elastomeric walls form an elongated chamber which resembles an elongated web in plan view. The outer elastomeric wall is protected by an outer cover. This tourniquet can be wrapped circumferentially about the limb at a location above the wound, and the marginal ends of the tourniquet are brought together with sufficient tension whereby when the marginal ends are suitably affixed to one another by a fastener means, the internal pressure of the tourniquet urges the inside wall surface against the limb with sufficient pressure to arrest loss of blood from the wound.

The fluid contained within the chamber is preferably a compressible fluid such as air, nitrogen, helium, or other suitably compressible gas including refrigerants such as "freeon".

In still another form of the invention, the chamber is filled with a non-compressible fluid, as for example a liquid of low viscosity such as water, a liquid of high viscosity such as oil, as well as some selected gels and the like.

More particularly, in the instance where the tourniquet is to be placed about one's finger, the tourniquet preferably is easily fastened into the form of a doughnut having an internal constant pressure slightly above 150 milimeters. The elastomeric sidewalls of the tourniquet preferably are fabricated in a manner to have a threshold pressure slightly above 150 milimeters pressure so that a proper predetermined constant pressure is maintained by the tourniquet against the finger, and the tourniquet is therefore urged thereagainst with sufficient pressure being effected on the finger to arrest bleeding from a wound. On the other hand, where an arm is wounded and bleeding, the tourniquet must be fabricated proportionally larger and have a chamber included therein wherein the sidewalls thereof are of a thickness and composition to provide a threshold pressure within the chamber of a value slightly above 250 milimeters pressure, which is the force which must be applied to the limb surface to arrest bleeding.

Where the tourniquet is to be applied to one's leg, the tourniquet is fabricated still larger, and the elastomeric material selected for the sidewall structure preferably is fabricated in a manner whereby the chamber pressure has a threshold value slightly above 300 milimeters so that the chamber wall is forced to bear against the blood vessels of the leg with a force which reduces bleeding to a minimum.

Accordingly, a primary object of the present invention is the provision of method and apparatus for arresting bleeding of a part of the anatomy associated with an animal, and especially a humanoid.

Another object of the present invention is the provision of method and apparatus by which an elastomeric chamber is placed circumferentially about part of a person's anatomy to thereby arrest flow of blood through the blood vessels contained therein.

A further object of this invention is the provision of a flexible structure which can be formed into a hollow toroidal tourniquet made of an elastomeric material which expands to provide a constant pressure therewithin so that when the toroidal chamber is placed about a person's limb, the surface of the toroidal wall bears against the outer surface of the limb with sufficient pressure to arrest bleeding.

A still further object of this invention is the provision of a tourniquet in the form of an elongated chamber having means by which the marginal ends thereof can be wrapped back and fastened upon themselves and thereby attach the tourniquet to one's limb, wherein the sidewall of the tourniquet is made of an elastomeric material which forms an internal chamber and which commences expanding at constant pressure when the internal pressure thereof is elevated to a value slightly above the blood pressure contained within the person's limb.

These and various other objects and advantages of the invention will become readily apparent to those skilled in the art upon reading the following detailed description and claims and by referring to the accompanying drawings.

The above objects are attained in accordance with the present invention by the provision of a method for use with apparatus fabricated in a manner substantially as described in the above abstract and summary.

BRIEF DESCRIPTION OF THE DRAWINGS

FIG. 1 is a fragmentary, perspective view of a person's limb having a tourniquet made in accordance with the present invention applied thereto;

FIG. 2 is a fragmentary view of another limb of a person, having a tourniquet made in accordance with the present invention applied thereto;

FIG. 3 is a perspective view of the embodiment of the tourniquet of FIG. 2 shown in combination with a pump means;

FIG. 4 shows the apparatus of FIGS. 2 and 3 in the inflated configuration;

FIG. 5 is an enlarged, cross-sectional view of the tourniquet disclosed in FIGS. 2-4;

FIG. 6 is an enlarged, perspective, fragmentary view showing the details of the tourniquet disclosed in FIGS. 2-6;

FIG. 7 is an enlarged, cross-sectional view of a tourniquet made in accordance with this invention;

FIG. 8 is a perspective view of a tourniquet made in accordance with this invention, with the tourniquet being in the inoperative configuration;

FIG. 9 is an opposite view of the tourniquet disclosed in FIG. 8;

FIG. 10 is a cross-sectional view which discloses the details of the apparatus of FIGS. 8 and 9;

FIG. 11 is a fragmentary view of the tourniquet disclosed in FIGS. 8-10, with some parts being broken away therefrom and some of the remaining parts being shown in cross-section;

FIG. 12 is a cross-sectional detail of the tourniquet of FIGS. 8-11;

FIG. 13 shows the tourniquet of FIG. 11 in another operative configuration; and, FIG. 14 sets forth an alternate embodiment of the tourniquet seen in FIG. 12.

DETAILED DESCRIPTION OF THE PREFERRED EMBODIMENTS

FIGS. 1 through 14 of the drawings disclose the preferred embodiments of a tourniquet apparatus made in accordance with the present invention. The tourniquet 10 or 110 is made into a rectangular configuration, and as shown in FIGS. 1-7, is arranged into the form of a doughnut or toroid when placed about a person's limb, such as seen at 12 in FIG. 1, or 112 in FIG. 2. The tourniquet is easily inflated with a pump means such as seen at 14 in FIG. 3.

Pump means 14 is connected to the tourniquet 10 by a small flexible conduit 16 affixed at 18 to the pump means 14. The pump means 14 includes the usual barrel 20 and plunger 22; and, the pump means can be an ordinary hypodermic syringe.

FIGS. 2, 4 and 6 of the drawings set forth another embodiment of a tourniquet apparatus 110 made in accordance with the present invention. The tourniquet 110 is fastened together at 24 by overlapping the marginal ends together as particularly illustrated in FIG. 6. As illustrated in FIGS. 7-9, together with other figures of the drawings, the fastener 24 preferably is a Velcro (TM) fastener means applied to one face of the tourniquet near the marginal end 26 thereof, with the other coacting Velcro fastener means being applied to the opposed face at the other marginal end 28 of the tourniquet. The fastener means at 24 is of the type which is releasably engaged in a manner known to those skilled in the art.

It will be noted in FIGS. 8 and 9 that the toruniquet has reinforced, parallel, spaced edges 30 and 32 which define the dimensions of the inflation chamber 34 as seen in FIG. 11. FIGS. 10-14 illustrate that an atmospheric chamber 36 is formed by the outermost wall surface 38 of the tourniquet. The atmospheric chamber 36 communicates with the ambient through small apertures 40 formed through wall surface 38.

The tourniquet wall surfaces 42 and 44 therefore cooperate together to form inflation chamber 34, while the atmospheric chamber 36 is formed by walls 38 and 42. The innermost wall 44 must be made from an elastomer of the proper thickness and modulus to achieve a transfer of the threshold pressure from chamber 34 onto the limb surface in order to properly arrest bleeding of a wound. The outer wall surface 42 of the chamber 34 preferably is made of an elastomeric material, similar to the innermost wall surface, which expands and maintains a constant pressure within the inflation chamber after the threshold pressure of the wall 42 is exceeded. The outermost wall 38 preferably is a self-supporting, corrugated surface which provides protection respective to the inflation chamber.

As seen in FIGS. 8-10, the opposed edges 30, 32 of the tourniquet preferably are fabricated in the manner set forth in the various figures of the drawings; however, it is also possible to heat weld the longitudinally extending marginal edges of members 38, 42, and 44 into sealed relationship respective to one another, for example, as seen in FIG. 12. It is preferred, however, to seal the opposed marginal edges of members 38, 42, and 44 together and attach the marginal edges within the illustrated C-shaped flexible elastic member seen at 32 in FIG. 10, thereby reinforcing the opposed marginal edges 30, 32 of the tourniquet. The opposed ends 26, 28 of members 38, 42, and 44 can be cemented together, or heat welded, to form the elongated inflation chamber 34 and the atmospheric chamber 36. The above mentioned C-shaped flexible elastic member at 32 has a connecting sidewall 54 affixed to opposed wall members 56 and 58. Wall members 54, 56, and 58 are made integrally and, as indicated by the arrow at numeral 60, clamp together the marginal ends 62, 64, and 66, respectively, of the outer wall surfaces 38, and the tourniquet wall surfaces 42 and 44, respectively.

In FIGS. 11 and 12, outer wall member 42 of inflation chamber 34 is free to expand toward and away from the outermost protective member 38. The outermost protective member 38 is preformed into the illustrated zig-zag cross-sectional configuration, best seen illustrated in the cross-sectional view of FIG. 12. Apertures 40 provide egress and ingress of ambient air respective to atmospheric chamber 36. It is essential that the innermost wall 44 of the inflation chamber 34 be sufficiently flexible so that it properly transfers pressure effected within the inflation chamber 34, through inner wall 44, and onto the surface of one's limb, with the pressure transfer being of a sufficient magnitude to arrest bleeding from the limb. It is also essential that the member 42 which forms the outer wall surface of the inflation chamber be fabricated from an elastomer of a selected thickness and modulus to cause the member 42 to commence expanding at substantially a constant pressure value, which is in excess of the pressure required to develop the force at wall 44 for preventing bleeding from the limb to which the tourniquet is attached. Therefore, it is essential that member 42 be provided with physical characteristics whereby the member expands at a threshold pressure which is in excess of the pressure required to prevent bleeding from a specific part of the anatomy for which the tourniquet is designed.

In FIGS. 13 and 14, the outermost protective member, or wall surface, 38 is convoluted, and is positioned to protect the inflation chamber outer wall 42 against reasonable hazards. In FIGS. 13 and 14, the edges 30, 32 are formed by the illustrated enlarged, longitudinally extending edge portions. The opposed edges 30, 32 must be sufficiently flexible to easily conform to one's limb when the tourniquet circumvents the limb and is attached thereto in the illustrated manner of FIGS. 1, 2, 4, 6, and 7. It is essential that member 44 correspond to the previously mentioned member 44 of the other figures of the drawings.

In FIG. 13, numeral 48 indicates the position of member 44 when the pressure within the inflation chamber is reduced to ambient. Numeral 50 indicates the outward deformation of innermost wall 44 when chamber 34 is suitably inflated with a fluid. Numeral 52 indicates the range of movement of wall surface 44. Wall 42 similarly moves in the opposite direction as the pressure within the inflation chamber is increased. The wall 42 must be fabricated from an elastomer having suitable characteristics for exhibiting a threshold pressure consistent with the blood pressure of the limb to which the tourniquet is to be applied. The innermost wall surface 44 of the inflation chamber must be sufficiently flexible to conform to one's limb and transfer the force within the inflation chamber onto the surface of the limb, so as to bear against the proper blood vessels in order to arrest bleeding from a wound located downstream thereof.

The apparatus of the present invention can be made in a number of different sizes so as to better accommodate different size people. The Velcro fastener at 24 can be utilized to advantageously provide a wide range of sizes according to the length of the marginal opposed ends that are provided with Velcro fastener material. Once the inflation chamber has been suitably inflated and placed in proper relative position respective to the wound, and blood vessels, it is unnecessary to further use the pump means 14, unless it is noted that the tourniquet has not been sufficiently inflated in order to completely arrest bleeding.

It is possible to inflate chamber 34 and store the tourniquet for subsequent use. However, during subsequent use of the tourniquet, should it be determined that insufficient pressure is effected onto the surface of the wounded limb, it is desirable to be able to increase the inflation pressure by an ordinary syringe 14. In this respect, it is preferred that the chamber 34 be inflated with compressible gas, although liquids can be used in lieu of the preferred inflation medium.

In use, several different sizes of apparatus made in accordance with the present invention are maintained readily available wherever an accident may be anticipated. The tourniquet apparatus preferably is provided in the form of one size adapted for use on a person's finger, another size adapted for use on a person's arm, and still another size adapted for use on a person's leg. It is therefore desirable to have available three distinct tourniquets of different design for the reason that the pressure requirements of the inflation chamber of each of the three tourniquets varies according to the location of the wound. For example, the blood pressure found in the veins of one's finger is quite different respective to the blood pressure found in one's leg or bicep. Therefore, the threshold pressure characteristics of the member 42 that forms the inflation chamber must be selected according to the anticipated use of the tourniquet.

In use, the previously inflated tourniquet is easily wrapped about the limb, with the opposed marginal ends thereof being overlapped respective to one another, so that the action of the Velcro fastener material removably fastens the opposed marginal ends together, thereby providing a toroidal tourniquet apparatus having almost or essentially a continuous pressure chamber formed therewithin. A tourniquet of the type disclosed herein provides an optimum pressure at the most optimum location of the limb for preventing significant bleeding from a wound. Those skilled in the art appreciate that there are many advantages in applying the exact amount of pressure required in order to arrest bleeding from a wound. A substantial amount of skill heretofore has been required in order to achieve the optimum desired pressure of a tourniquet applied to a limb. The present invention provides a means and a method by which almost any layman can rapidly and efficiently apply a tourniquet to a wounded limb and thereby achieve the optimum pressure required to prevent significant loss of blood from the wound.

Those skilled in the art, having digested this disclosure, will appreciate that the tourniquet of this invention enables a wounded person to receive one or more tourniquets on one or more limbs that may be wounded, wherein the tourniquets each have the unexpected advantage of optimumly resisting the flow of blood from the wounded limb, and thereby enables the wounded patient to be safely transported to the hospital or emergency center for proper care and treatment. Such a novel tourniquet has heretofore been unavailable.

It is contemplated to prepare a rubber compound which is to be made into a tourniquet according to the embodiment of the invention illustrated in the figures of the drawings. The sidewalls of the tourniquet will have a modulus of elasticity and thickness to give a calculated threshold pressure for preventing bleeding from a blood vessel having a blood pressure as follows:

A. 100 mm pressure
B. 150 mm pressure
C. 200 mm pressure.

Example II. The above rubber compound —A— is to be made into a tourniquet according to the embodiment of FIGS. 3, 4, 5 and 7. The tourniquet is contemplated to be three and one-half inches overall length, one-half inch wide, and three-eights inch thick. The Velcro fastener at 24 is made to extend about five-eights inches either side of the inflation chamber to thereby enable the effective diameter of the tourniquet to be adjusted to accommodate a large range of various sized fingers. The thickness of the sidewalls of the elastomer is to be selected to provide sufficient pressure against the finger to enable the tourniquet to be used to arrest bleeding from a vein having 100 mm blood pressure.

Example III. It is contemplated to employ a larger tourniquet, such as seen illustrated in FIGS. 1 and 7, for use about one's arm. The elastomeric material of the inflation chamber is selected to prevent bleeding of a vein carrying 150 mm blood pressure, and therefore, the above elastomer —B— is selected for wall 42.

Example IV. The tourniquet of FIG. 1 is made of the compound —C— and is inflated beyond the threshold pressure and stored until needed. The tourniquet is placed about one's leg and positioned above a wound, whereupon, bleeding is arrested.

The tourniquet of this invention can previously be inflated to the threshold pressure prior to being positioned above the wound. When the tourniquet is used, sufficient tension can be applied to the tourniquet by proper adjustment of the fasteners at 26 and 28, which are mutually engaged in overlapping relationship respective to one another.

We claim:

1. A constant pressure tourniquet of a size to be removably received about a person's limb; said tourniquet includes spaced wall surfaces made of an elastomeric material; said wall sur faces form an inflation chamber therewithin;

said elastomeric material of at least one wall surface has a thickness and modulus of elasticity that exhibits a threshold pressure which is slightly greater than the blood pressure of the vessels of the limb to which the tourniquet may be attached; whereby, inflation of the tourniquet to a volume greater than the volume attained at the threshold pressure of the elastomeric material causes the tourniquet to apply a substantially constant pressure to the limb and thereby arrest flow of blood from a wound that may be associated with the limb.

2. The tourniquet of claim 1 wherein said chamber contains a compressible fluid, and further including means by which compressible fluid can be added to said chamber.

3. The tourniquet of claim 1 wherein said chamber contains an incompressible fluid, and further including means by which an incompressible fluid can be added to the chamber.

4. The tourniquet of claim 1 wherein said tourniquet is an elongated, relatively flat member having fastener means at the marginal ends thereof so that said wall surfaces form a toroidal chamber when the tourniquet is applied to one's limb, and further including means by which compressible fluid can be added to said chamber.

5. The tourniquet of claim 4 and further including a protective outermost wall surface for protecting the outer wall of said inflation chamber; and wherein said inflation chamber contains an incompressible fluid, and further including means by which incompressible fluid can be added to said chamber.

6. The tourniquet of claim 1 wherein said wall surfaces which form the inflation chamber include opposed longitudinally extending sides joined at opposed ends thereof which provides an elongated said chamber; fastener means by which said opposed ends can be fastened together, with the tourniquet extending about a limb of a person; said tourniquet further includes an outermost protective wall having longitudinal edges attached to the longitudinal edges of the inflation chamber wall surface.

7. The tourniquet of claim 6 wherein the elongated chamber contains an incompressible fluid, and further including means by which incompressible fluid can be added to said chamber.

8. The tourniquet of claim 6 wherein said chamber contains an incompressible fluid, and further including means by which compressible fluid can be added to said chamber.

9. A tourniquet comprising an elastomeric body adapted to circumscribe a person's limb and exert sufficient compressive force thereon to arrest the flow of blood through a vein found in the limb;

said body includes spaced elongated wall surfaces which are joined along the peripheral edges thereof and form an expansible enclosure within which a fluid is contained to thereby provide a pressure therein above ambient;

the elastomeric material of at least one of said wall surfaces has a thickness and modulus of elasticity which maintains substantially a constant pressure within said enclosure when the pressure within said enclosure is elevated to a value greater than the threshold value of the elastomeric material and greater than the blood pressure within the vein of the limb to which the tourniquet is to be attached.

10. The tourniquet of claim 9 wherein said wall surfaces include opposed longitudinally extending sides and opposed ends joined together to form an elongated chamber therewithin, fastener means by which the marginal opposed ends of the tourniquet can be fastened together and about a limb of a person, thereby providing a discontinuous toroidal chamber.

11. The tourniquet of claim 10 wherein said chamber contains a compressible fluid, and further including means by which compressible fluid can be added to said chamber.

12. The tourniquet of claim 10 wherein said chamber contains an incompressible fluid, and further including means by which incompressible fluid can be added to said chamber.

13. The tourniquet of claim 9 wherein said wall surface forms a discontinuous toroidal chamber, and wherein said chamber contains an incompressible fluid, and further including means by which incompressible fluid can be added to said chamber.

14. The tourniquet of claim 9 wherein there is further included means forming a protective outermost wall surface for protecting the outer wall of said inflation chamber; and wherein said inflation chamber contains an incompressible fluid, and further including means by which incompressible fluid can be added to said chamber.

15. Method of arresting the flow of blood through the blood vessels of an animal, comprising the steps of:
   (1) forming a chamber within which fluid can be isolated by building an elongated enclosure having opposed spaced wall surfaces made of an elastomer.
   (2) selecting the thickness and modulus of elasticity of one of the elastomer walls whereby a constant pressure is realized within said chamber when the pressure therein slightly exceeds the blood pressure of the animal as the threshold pressure of the elastomer wall is exceeded;
   (3) encirculating a limb of the animal with the elastomeric chamber at a location upstream of the area where the flow through the blood vessels of the animal is to be arrested.

16. The method of claim 15 and further including the step of filling said chamber with a compressible fluid.

17. The method of claim 15 and further including the step of filling said chamber with an incompressible fluid.

18. The method of claim 15 and further including the step of making said continuous wall surface into the form of an elongated chamber; and, arranging fastener means by which the opposed ends of the tourniquet can be fastened together and about a limb of a person.

* * * * *